United States Patent [19]

McCandlish et al.

[11] 4,337,232

[45] Jun. 29, 1982

[54] AMMONIA SYNTHESIS PROCESS USING MOLYBDENUM OXYCARBONITRIDE CATALYST

[75] Inventors: Larry E. McCandlish, Highland Park; Edwin L. Kugler, Summit, both of N.J.

[73] Assignee: Exxon Research & Engineering Co., Florham Park, N.J.

[21] Appl. No.: 243,824

[22] Filed: Mar. 16, 1981

[51] Int. Cl.$^3$ .............................................. C01C 1/04
[52] U.S. Cl. .................................................... 423/362
[58] Field of Search ........................................ 423/362

[56] References Cited

U.S. PATENT DOCUMENTS

| 3,492,100 | 4/1970 | Pierre et al. | |
|---|---|---|---|
| 3,872,136 | 7/1975 | Middelhoek et al. | |
| 4,128,621 | 12/1978 | Homeier | 423/362 |
| 4,163,775 | 8/1979 | Foster et al. | 423/362 |
| 4,239,536 | 12/1980 | Yamamoto et al. | |
| 4,271,041 | 6/1981 | Boudart et al. | 423/362 |

FOREIGN PATENT DOCUMENTS

| 4134719 | 4/1978 | Japan . |
| 53-10692 | 6/1978 | Japan . |
| 5031517 | 8/1978 | Japan . |

OTHER PUBLICATIONS

Izv. Akad. Nauk. SSSR, Neorg. Mater. 1976, 12(9), 1581–1584.
Bureau of Mines Report of Investigation #6974 (Jul. 1976) by J. F. Schultz, F. S. Karn and R. B. Anderson entitled "Noble Metals, Molybdenum and Tungsten in Hydrocarbon Synthesis".
Nature pp. 1327–1328 (Jun. 1964).
Le Clercq et al. "Preparation of Catalyst II", Elsevier Sci. Publ. 3, 627 (1979).
Boudart et al. "Seventh International Congress on Catalysis", Tokyo, Jul. 3–4 (1980), Preprint A-40.
Kirk–Othmer, *Encyclopedia of Chemical Technology*, Second Edition, vol. 2, Interscience Publishers, (1963) pp. 271–272.

*Primary Examiner*—O. R. Vertiz
*Assistant Examiner*—Wayne A. Langel
*Attorney, Agent, or Firm*—Robert J. North

[57] ABSTRACT

A process for synthesizing ammonia is described wherein a mixture of nitrogen and hydrogen is contacted with novel molybdenum oxycarbonitride catalyst.

7 Claims, No Drawings

AMMONIA SYNTHESIS PROCESS USING MOLYBDENUM OXYCARBONITRIDE CATALYST

BACKGROUND OF THE INVENTION

1. Field of the Invention

This invention relates to a process for synthesizing ammonia by contacting mixtures of hydrogen and nitrogen with novel molybdenum oxycarbonitride catalyst.

2. Brief Description of the Prior Art

The synthesis of ammonia from contacting mixtures of hydrogen and nitrogen with a suitable catalyst is well-known in the art. Examples of such processes are the Haber process, modified Haber-Bosch process, Claude process, Casale process, Fauser process and Mont Cenis process. At present, all of these processes generally utilize promoted iron catalysts.

There is a constant search in the field for new types of catalysts and catalyst combinations which will catalyze the reaction between hydrogen and nitrogen to form ammonia that are potentially less expensive, give better conversions, have greater longevity and better catalyst selectivity and activity.

SUMMARY OF THE INVENTION

We have found that a novel composition, molybdenum oxycarbonitride, is an effective and highly active catalyst in the synthesis of ammonia from gaseous mixtures of hydrogen and nitrogen. In particular, high rates of ammonia production at one atmosphere can be obtained relative to other processes using commercially available iron-based catalysts.

In accordance with this invention, there is provided a process for synthesizing ammonia comprising contacting a gaseous mixture of hydrogen and nitrogen, in about a 1:3 to 10:1 volume ratio, respectively, with a catalyst comprised of molybdenum oxycarbonitride in a temperature range of about 300°–500° C., a pressure of about 0.1 to 20 MPa, and a space velocity of about 1000 to 60,000 v/v/hr., thereby resulting in product ammonia.

DESCRIPTION OF THE INVENTION AND PREFERRED EMBODIMENTS

The novel composition, molybdenum carbonitride, is a subject of a co-pending application, Ser. No. 209,998, filed Nov. 24, 1980, which describes the properties of the material, structure, distinguishing physical characteristics, methods of preparation, use as an abrasive and the like, and which is hereby incorporated by reference for that purpose.

The subject invention process is a process for utilizing said molybdenum oxycarbonitride catalyst in producing synthetic ammonia from mixtures of hydrogen and nitrogen.

We have unexpectedly found that molybdenum oxycarbonitride is a very effective catalyst for ammonia synthesis. The reason why this material is an active catalyst for the process, as compared to known Group VIII catalysts, is not clearly understood.

The molybdenum oxycarbonitride composition useful as a catalyst in the subject process is thoroughly described in the above-identified incorporated reference and preferably has a particle size of less than about 100 Å, as evidenced by a measured surface area of about 10 to 160 m$^2$/gram (as measured by the well-known BET argon method and X-ray diffraction line broadening). However, molybdenum oxycarbonitride having larger and smaller surface area than that described above, are also applicable in the subject process.

Generally, the catalyst is initially used in the passivated form, which is relatively stable in air, to avoid decomposition. The catalyst is then generally heat treated in a reducing atmosphere to generate the reduced catalyst form prior to reaction.

The above-identified reference readily discloses a general procedure for producing the passivated form of molybdenum oxycarbonitride.

The empirical formula of the molybdenum oxycarbonitride is $MoO_aC_bN_c$, wherein a, b and c are non-zero decimal values and wherein the sum of $a+b+c$ is less than or equal to about one. A preferred composition for use in the process is: $MoO_{0.41}C_{0.31}N_{0.33}$, produced, for example, from the thermal decomposition of ethylenediammonium molybdate at about 650° C. under a helium atmosphere.

The catalyst composition also can be unsupported or supported on conventional materials which are inert under the process conditions. Representative examples of suitable supports are alumina, silica, titania, magnesia, carbon and the like. If supported, the catalyst support can be present in conventional amounts.

Representative types of reactors and apparatus that can be employed in the process are glass and stainless steel reactors that are vertical, horizontal or down-flow types which utilize the catalyst as a fixed bed, fluid bed, slurry and the like. Preferred type of apparatus is a fixed bed.

The catalyst is generally pretreated at an elevated temperature in a reducing atmosphere for a period of time prior to the process. The temperature, atmosphere and time required are conventional in the art. A set of conditions which was found to be effective was pretreatment at 450° C. in a hydrogen atmosphere, at a space velocity of about 10,000 v/v/hr. for a time of about 2 hours. Other sets of conditions will be obvious to one skilled in the art.

The process is conducted by contacting a mixture of hydrogen and nitrogen gas with the above-described molybdenum oxycarbonitride catalyst under the conditions described herein and collecting product ammonia.

The gaseous mixture of hydrogen/nitrogen used is in the volume ratio of about 1:3 to 10:1 and preferably the ratio is about 3:1.

The temperature of the process is conducted in the range of about 300° to 500° C. and preferably about 350° to 450° C.

The pressure of the gaseous feedstream in the process is carried out in the region of about 0.1 to 20 MPa and preferably 2 to 15 MPa (1 atmosphere being equivalent to 0.1 MPa).

The space velocity of the process is carried out in the range of about 1000 to 60,000 v/v/hr. and preferably about 5000 to 50,000 v/v/hr.

Product ammonia in the process is collected, separated and purified by conventional methods in the art.

Other modifications of the subject process will become apparent to one skilled in the art from a reading of this disclosure.

The following examples are illustrative of the best mode of carrying out the invention as contemplated by us and should not be construed as being limitations on the scope and spirit of the instant invention.

EXAMPLE 1

A 1.0 gram sample of passivated molybdenum oxycarbonitride (of approximate empirical formula: $MoO_{0.41}C_{0.31}N_{0.33}$ and BET argon surface of about 130 m²/g.) was reduced as a fixed bed catalyst in a 3:1 mixture of $H_2/N_2$ under 0.1 MPa of pressure for a period of about four hours in a glass reactor system. The run was carried out at three different temperatures of about 450° C., 400° C. and then about 350° C. The gas hourly space velocity was run at five different rates of 1200, 2400, 3600, 4800 and 6000 v/v/hr. for each temperature used. The rate of ammonia production and the volume percent ammonia in the product stream, as determined by gas chromatography and wet chemical methods are also given below in Table I.

TABLE I
AMMONIA SYNTHESIS ACTIVITY OF MOLYBDENUM OXYCARBONITRIDE

| Temp. °C. | Pressure (MPa) | GHSV (v/v/hr) | Rate[a] (micromoles/min/g) | % $NH_3$[b] |
|---|---|---|---|---|
| 450 | 0.11 | 1200 | 1.77 | 0.198 |
| 450 | 0.11 | 2400 | 3.30 | 0.185 |
| 450 | 0.11 | 3600 | 4.63 | 0.173 |
| 450 | 0.11 | 4800 | 6.00 | 0.168 |
| 450 | 0.11 | 6000 | 7.44 | 0.167 |
| 400 | 0.11 | 1200 | 1.72 | 0.193 |
| 400 | 0.11 | 2400 | 2.80 | 0.157 |
| 400 | 0.11 | 3600 | 3.68 | 0.137 |
| 400 | 0.11 | 4800 | 4.04 | 0.113 |
| 400 | 0.11 | 6000 | 4.38 | 0.098 |
| 350 | 0.11 | 1200 | 0.72 | 0.081 |
| 350 | 0.11 | 2400 | 1.17 | 0.066 |
| 350 | 0.11 | 3600 | 1.46 | 0.055 |
| 350 | 0.11 | 4800 | 1.73 | 0.049 |
| 350 | 0.11 | 6000 | 2.14 | 0.048 |

[a]rate of $NH_3$ production
[b]volume percent $NH_3$ in product gaseous stream

As is seen from the data, appreciable rates of $NH_3$ formation can be obtained over a fairly broad combination of process temperatures and space velocities.

EXAMPLE 2

A 2.0 gram sample of passivated molybdenum oxycarbonitride (from the same stock of material as described in Example 1) was reduced in a 3:1 volume mixture of $H_2/N_2$ at a gas hourly space velocity of 2400 v/v/hr. for a period of four hours in a stainless steel reactor. The temperature was run at three values: 450° C., 400° C. and 350° C. and the pressure was adjusted to 0.1, 1.0 and 2.0 MPa for each temperature run. Results are given below in Table II.

TABLE II
AMMONIA SYNTHESIS ACTIVITY OF MOLYBDENUM OXYCARBONITRIDE

| Temp. °C. | Pressure (MPa) | GHSV (v/v/hr) | Rate[a] (micromoles/min/g) | % $NH_3$[b] |
|---|---|---|---|---|
| 450 | 0.11 | 2400 | 2.95 | 0.18 |
| 450 | 1.00 | 2400 | 11.85 | 0.73 |
| 450 | 2.00 | 2400 | 17.85 | 1.16 |
| 400 | 0.11 | 2400 | 2.10 | 0.13 |
| 400 | 1.03 | 2400 | 7.20 | 0.44 |
| 400 | 2.04 | 2400 | 9.35 | 0.58 |
| 350 | 0.11 | 2400 | 1.25 | 0.08 |
| 350 | 1.01 | 2400 | 3.90 | 0.24 |
| 350 | 2.02 | 2400 | 5.45 | 0.34 |

[a]rate of $NH_3$ production
[b]volume percent $NH_3$ in product gaseous stream

As seen from the data, increasing pressure in the process significantly increases the rate of $NH_3$ production at constant space velocity.

What is claimed is:

1. A process for synthesizing ammonia comprising contacting a gaseous mixture of hydrogen and nitrogen, in a 1:3 to 10:1 volume ratio, respectively, with a catalyst comprised of molybdenum oxycarbonitride, at a temperature in the range of about 300° to 500° C., a pressure of about 0.1 to 20 MPa, and a space velocity of about 1000 to 60,000 v/v/hr., thereby resulting in product ammonia.

2. The process of claim 1 wherein said molybdenum oxycarbonitride is of the formula: $MoO_aC_bN_c$, wherein a, b, and c are non-zero decimal values and wherein the sum of a+b+c is less than or equal to about one.

3. The process of claim 1 wherein said molybdenum oxycarbonitride possess a BET surface area of about 10 to 160 m²/g.

4. The process of claim 1 wherein said temperature is about 350° to 450° C.

5. The process of claim 1 wherein said pressure is about 2 to 15 MPa.

6. The process of claim 1 wherein said space velocity is about 5,000 to 50,000 v/v/hr.

7. The process of claim 1 wherein said volume ratio of hydrogen to nitrogen is about 3:1.

* * * * *